(12) United States Patent
Dwivedi et al.

(10) Patent No.: US 8,829,186 B2
(45) Date of Patent: Sep. 9, 2014

(54) METHOD FOR PREPARATION OF PITAVASTATIN AND PHARMACEUTICAL ACCEPTABLE SALTS THEREOF

(71) Applicant: Cadila Healthcare Limited, Gujarat (IN)

(72) Inventors: Shriprakash Dhar Dwivedi, Gujarat (IN); Dhimant Jasubhai Patel, Gujarat (IN); Alpesh Pravinchandra Shah, Gujarat (IN); Brij Khera, Princeton, NJ (US)

(73) Assignee: Cadila Healthcare Limited, Ahmedabad (IN)

( * ) Notice: Subject to any disclaimer, the term of this patent is extended or adjusted under 35 U.S.C. 154(b) by 0 days.

(21) Appl. No.: 13/665,932

(22) Filed: Nov. 1, 2012

(65) Prior Publication Data
US 2013/0059885 A1 Mar. 7, 2013

Related U.S. Application Data

(62) Division of application No. 13/009,492, filed on Jan. 19, 2011, now abandoned.

(30) Foreign Application Priority Data

Jan. 20, 2010 (IN) .......................... 159/MUM/2010

(51) Int. Cl.
*C07D 215/14* (2006.01)
(52) U.S. Cl.
CPC .................................... *C07D 215/14* (2013.01)
USPC ............................................ 546/10; 546/173
(58) Field of Classification Search
None
See application file for complete search history.

(56) References Cited

U.S. PATENT DOCUMENTS

| 2009/0176987 A1* | 7/2009 | Ohara et al. ................... 546/173 |
| 2009/0275752 A1* | 11/2009 | Reddy et al. ................... 544/297 |
| 2012/0016129 A1* | 1/2012 | Satyanarayana Reddy et al. ............................ 546/173 |

FOREIGN PATENT DOCUMENTS

| WO | 2007125547 A2 | 11/2007 |
| WO | 2007132482 A2 | 11/2007 |

OTHER PUBLICATIONS

Berge et al., Pharmaceutical Salts, 66(1) J. Pharma. Science, 1-19 (1977).*
Acemoglu et al., A New and Efficient Synthesis of the HMG-CoA Reductase Inhibitor Pitavastatin, 90(6) Helvetica Chimica Acta 1069-1081 (2007).*
Takahashi et al., "Synthesis of an Artificial HMG-CoA Reductase Inhibitor NK-104 via a Hyrosilylation-Cross-Coupling Reaction" Bull. Chem. Soc. Jpn. 68(9):2649-2656 (1995).
Suzuki M et al; "Synthesis and Biological Evaluations of Quinoline-based HMG-CoA Reductase Inhibitors", Bioorganic & Medicinal Chemistry, Pergamon, GB, vol. 9, No. 10, Jan. 1, 2001, pp. 272727-272743.
Takahashi K et al: "A New Synthesis of HMG-CoA Reductase Inhibitor NK-104 Through Hydrosilylation-Cross Coupling Reacation", Tetrahedron Letters, Elsevier, Amsterdam, NL, vol. 34, No. 51, Jan. 1, 1993, pp. 8263-8266.
Hiyama T et al: "Synthesis of Artificial HMG-CoA Reductase Inhibitors Based on the Olefination Strategy", Bulletin of the Chemical Society of Japan, Chemical Society of Japan, Tokyo, Japan, vol. 68, No. 1, Jan. 1, 1995, pp. 364-372.
European Patent Office acting as the International Search Authority under the Patent Cooperation Treaty, International Search Report, PCT/IN2011/000039, Oct. 28, 2011.

* cited by examiner

*Primary Examiner* — Janet L Andres
*Assistant Examiner* — Timothy R Rozof
(74) *Attorney, Agent, or Firm* — Brij Khera; William D. Hare, Esq.; McNeely, Hare & War, LLP

(57) ABSTRACT

The present invention discloses a compound, which is alkali or alkaline earth metal salts of pitavastatin, wherein the alkali or earth metal comprise one or more of magnesium, zinc, potassium, strontium and barium.

30 Claims, 4 Drawing Sheets

Figure 1:
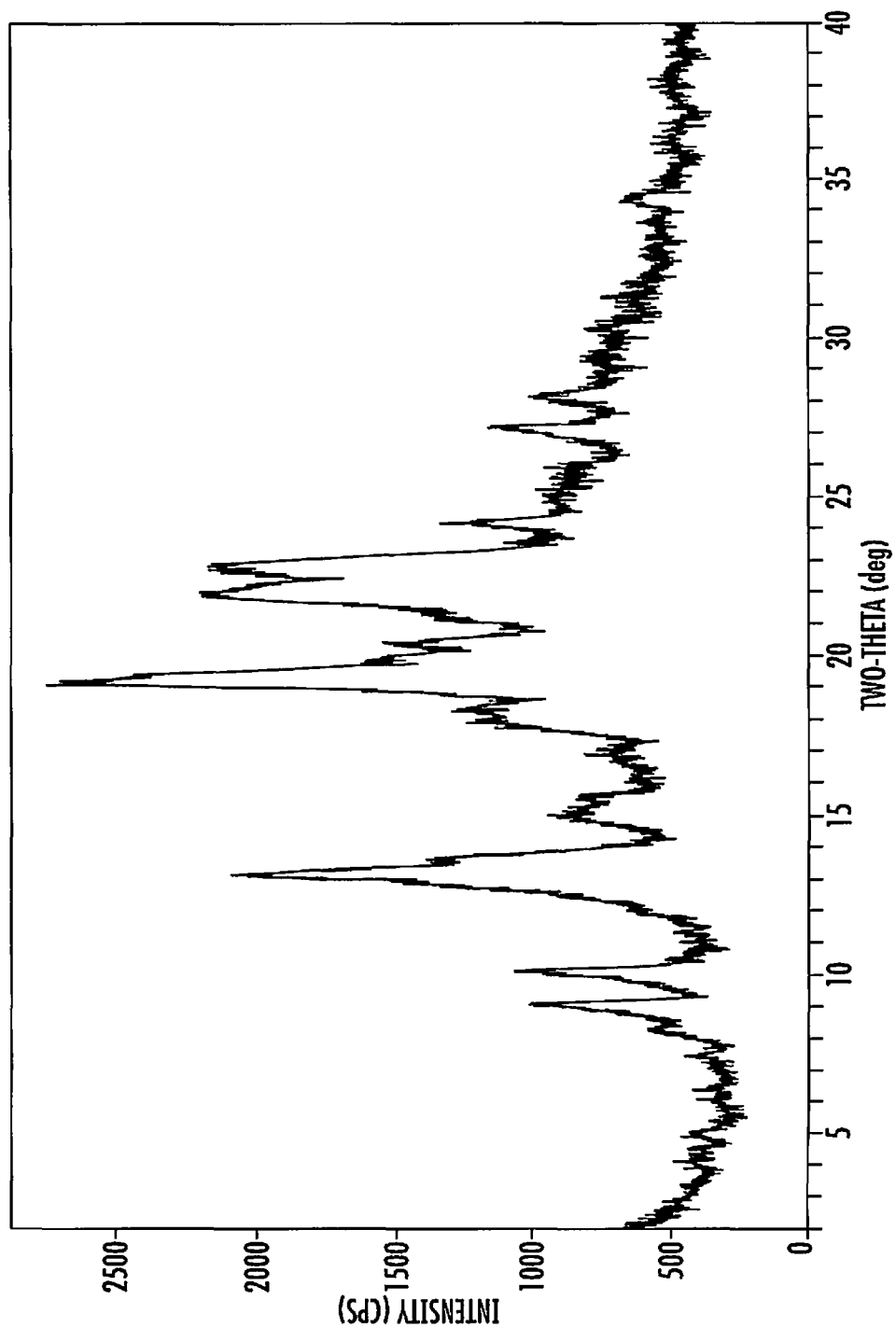

METHOD FOR PREPARATION OF PITAVASTATIN AND PHARMACEUTICAL ACCEPTABLE SALTS THEREOF

FIELD OF THE INVENTION

The present invention relates to processes for the preparation of pitavastatin and pharmaceutically acceptable salts thereof. In particular, the present invention provides processes for the preparation of pitavastatinalkali or alkaline earth metal salts in crystalline and amorphous forms.

BACKGROUND OF THE INVENTION

Pitavastatin calcium is chemically known as (3R,5S)-7-[2-cyclopropyl-4-(4-fluorophenyl)quinolin-3-yl]-3,5-dihydroxy-6(E)-heptenoic acid calcium salt having the formula IA is known in the literature.

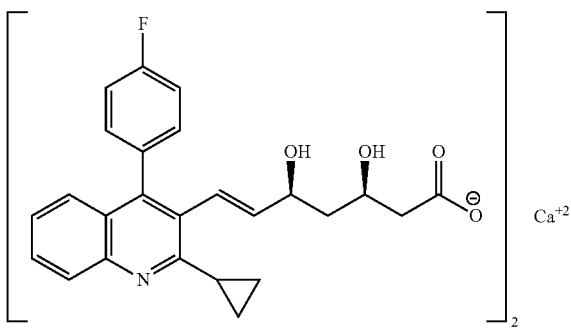

(IA)

Pitavastatin is a synthetic lipid-lowering agent that acts as an inhibitor of 3-hydroxy-3-methylglutaryl-coenzyme a (HMG-CoA) reductase (HMG-CoA Reductase inhibitor). This enzyme catalyzes the conversions of HMG-CoA to mevalonate, inhibitors are commonly referred to as "statins". Statins are therapeutically effective drugs used for reducing low density lipoprotein (LDL) particle concentration in the blood stream of patients at risk for cardiovascular disease. Pitavastatin is used in the treatment of hyperchloesterolemia and mixed dyslipidemia.

Pitavastatin calcium has recently been developed as a new chemically synthesized and powerful statin by Kowa Company Ltd, Japan. On the basis of reported data, the potency of Pitavastatin is dose-dependent and appears to be equivalent to that of Atorvastatin. This new statin is safe and well tolerated in the treatment of patients with hypercholesterolaemia. Significant interactions with a number of other commonly used drugs can be considered to be extremely low.

Processes for the preparation of Pitavastatin are described in EP-A-0304063 and EP-A-1099694 and in the publications by N. Miyachi et al. in Tetrahedron Letters (1993) vol. 34, pages 8267-8270 and by K. Takahashi et al. in Bull. Chem. Soc. Japan (1995) Vol. 68, 2649-2656. These publications describe the synthesis of Pitavastatin in great detail but do not describe the hemi-calcium salt of Pitavastatin. The publications by LA. Sorbera et al. in Drugs of the Future (1998) vol. 23, pages 847-859 and by M. Suzuki at al. in Bioorganic & Medicinal Chemistry Letters (1999) vol. 9, pages 2977-2982 describe Pitavastatin calcium, however, a precise procedure for its preparation is not given. A full synthetic procedure for the preparation of Pitavastatin calcium is described in EP-A-0520406. In the process described in this patent Pitavastatin calcium is obtained by precipitation from an aqueous solution as a white crystalline material with a melting point of 190-192° C.

US20090182008 A1 discloses polymorphic form A, B, C, D, E, and F, and the amorphous form of Pitavastatin Calcium salt (2:1). In particular, crystalline Form A having water content from about 5% to about 15% and process for its preparation are disclosed.

US20090176987 A1 also discloses polymorphic form crystal form A of Pitavastatin Calcium which contains from 5 to 15% of water and which shows, in its X-ray powder diffraction as measured by using CuKα radiation, a peak having a relative intensity of more than 25% at a diffraction angle (2θ) of 30.16°.

WO2007/132482 A1 discloses a novel process for the preparation of Pitavastatin Calcium by condensing bromide salt of formula-3 with aldehyde compound of formula-4 to obtain olefinic compound of formula-5 and converting olefinic compound to Pitavastatin Calcium via organic amine salt for purification.

There are no reports available in the prior art for the preparation of Pitavastatin Magnesium. Thus, the inventors of the present inventions provide a novel pharmaceutically acceptable salt of Pitavastatin, preferably magnesium salt.

SUMMARY OF THE INVENTION

In accordance with the present invention, there is provided alkali or alkaline earth salt of quinoline derivatives such as pitavastatin, a HMG-CoA inhibitors, more specially, the present invention provides a novel process for the preparation of pitavastatinmagnesium it is crystalline and amorphous form.

In one embodiment, there is provided a novel process for the preparation of pitavastatin and its pharmaceutically acceptable salts. In particular, pitavastatinalkali or alkaline earth metal comprises one or more of magnesium, zinc, potassium, strontium, barium and the like. Pitavastatin, which is chemically known as (3R,5S)-7-[2-cyclopropyl-4-(4-fluorophenyl)quinolin-3-yl]-3,5-dihydroxy-6(E)-heptenoic acid and its pharmaceutically acceptable salts having the general formula I

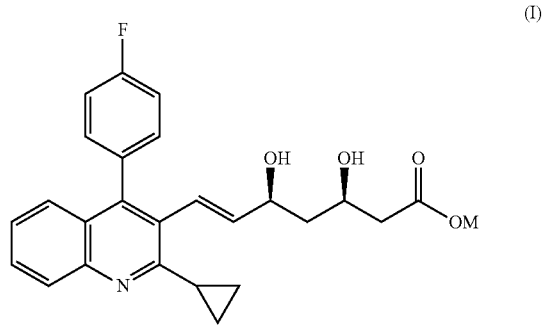

(I)

wherein, M is $K^+$, $Mg^{+2}$, $Sr^{+2}$, $Zn^{+2}$, $Ba^{+2}$.

In one preferred embodiment, there is provided a novel process for the preparation of pitavastatin and its pharmaceutically acceptable salts, particularly pitavastatinmagnesium which is chemically known as (3R,5S)-7-[2-cyclopropyl-4-(4-fluorophenyl)quinolin-3-yl]-3,5-dihydroxy-6(E)-heptenoic acid Magnesium salt having the formula IB.

In second embodiment, there is provided a novel salt, pitavastatinmagnesium of Formula (IB)

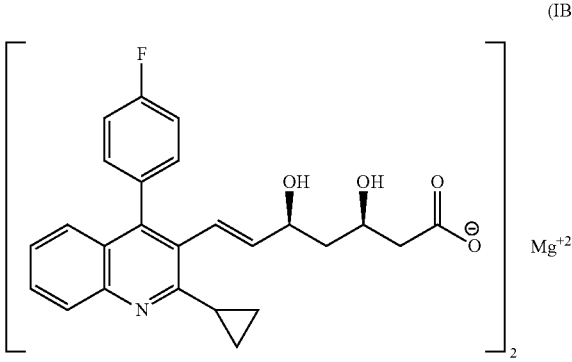

(IB)

In yet another embodiment, there is provided pitavastatinmagnesium it its crystalline form having X-ray powder diffraction peaks at 10.1, 13.2, 19.3 and 27.2±0.2 (2θ).

In further embodiment, there is provided a process for the preparation of pitavastatinmagnesium of formula (1B), the process comprising:
(a) reacting phosphonium bromide compound of Formula-IV with an aldehyde compound of Formula-III in the presence of an alkali or alkaline earth metal base in one or more suitable polar aprotic solvent to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of formula-II;
(b) hydrolyzing the compound of Formula-II under the acidic conditions to remove the acetonide protection to form a diol compound;
(c) treating the diol compound of step (b) in-situ with an alkali metal hydroxide to form the corresponding alkali metal salt of pitavastatin (I);
(d) treating alkali metal salt of pitavastatin with a magnesium source to obtain pitavastatinmagnesium; and
(e) isolating the pitavastatinmagnesium.

According to the embodiments, the process for the preparation of pitavastatinmagnesium according to the present inventions provides crystalline form of pitavastatinmagnesium having water content in the range of from about 7% to about 12% wt/wt.

According to another embodiment, the compound (4R, 6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester of formula (II) in crystalline form.

According to another embodiment, there is provided an improved process for the purification of (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester of formula (II) to obtain in crystalline form.

According to the further embodiments, there is provided a process for the preparation of pitavastatinmagnesium in amorphous form, the process comprising:
(a) providing a solution comprising pitavastatinmagnesium in a suitable organic solvent wherein the organic solvent is one or more of a chlorinated solvent, alcoholic solvent, ketonic solvent, aliphatic or cyclic ether and mixtures thereof;
(b) adding suitable antisolvent to the solution; and
(c) recovering the amorphous form of the pitavastatinmagnesium.

According to the further embodiments, there is provided a process for the preparation of an amorphous form of the pitavastatinmagnesium having water content less than about 2% wt/wt,
the process comprising:
(a) providing pitavastatinmagnesium in crystalline form having water content in the range of about 8% to about 12% wt/wt;
(b) contacting the pitavastatinmagnesium with humid air in a fluidized bed drier, or maintaining the pitavastatinmagnesium at a temperature of from about 5 to about 60° C., under pressure of less than 30 mm/Hg for a period of from about 1 to 5 days; and
(c) recovering the pitavastatinmagnesium in the amorphous form having water content less than about 2% wt/wt.

According to the further embodiment, there is provided substantially pure pitavastatinmagnesium in stable crystalline form.

DETAILED DESCRIPTION OF DRAWINGS

FIG. 1: X-ray diffraction pattern of crystalline pitavastatinmagnesium having about 8% to about 12% water content prepared as per the process of Example-2

Figure 2:
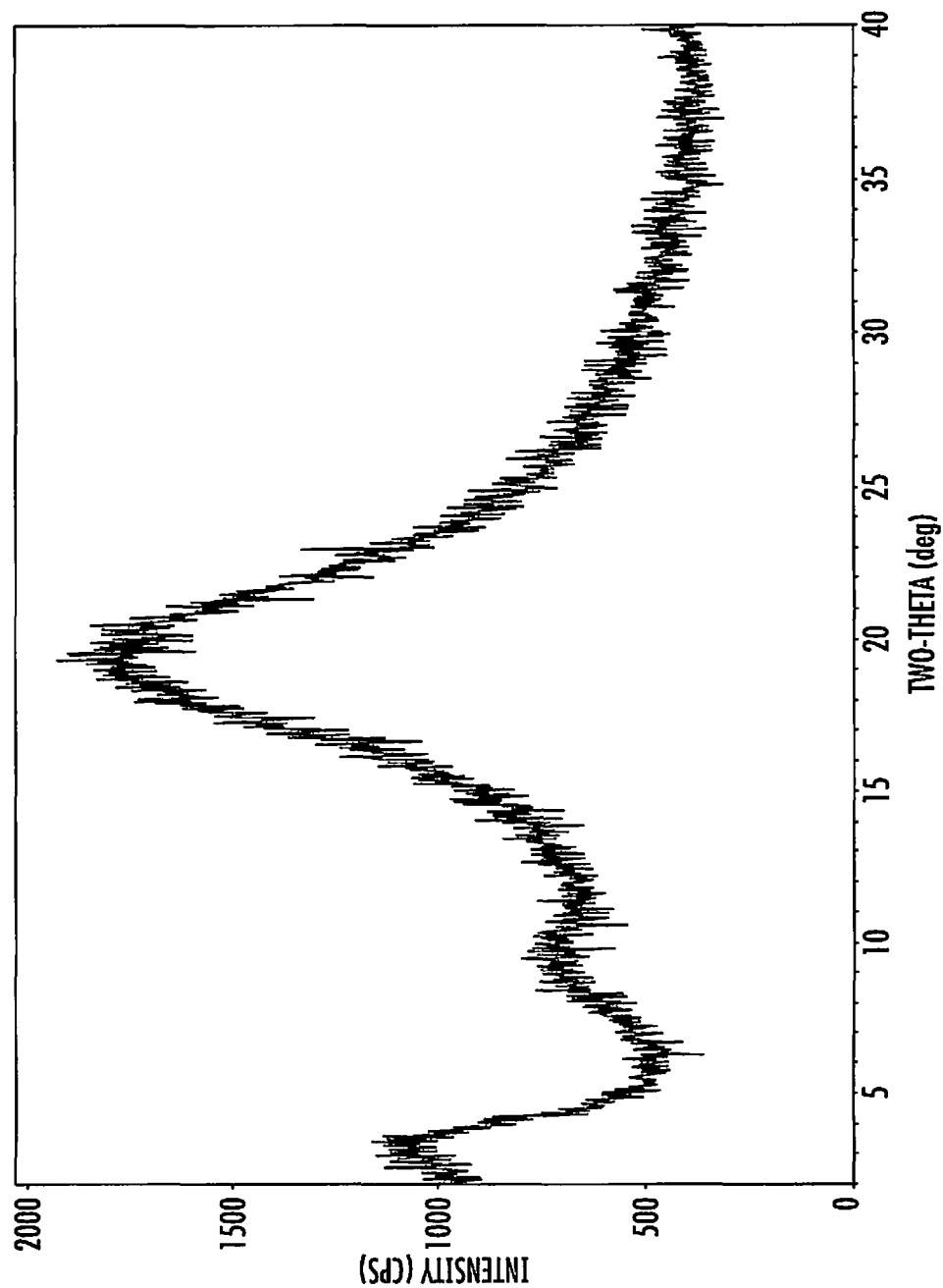

FIG. 2: X-ray diffraction pattern of amorphous pitavastatinmagnesium prepared as per the process of Example-3

Figure 3:
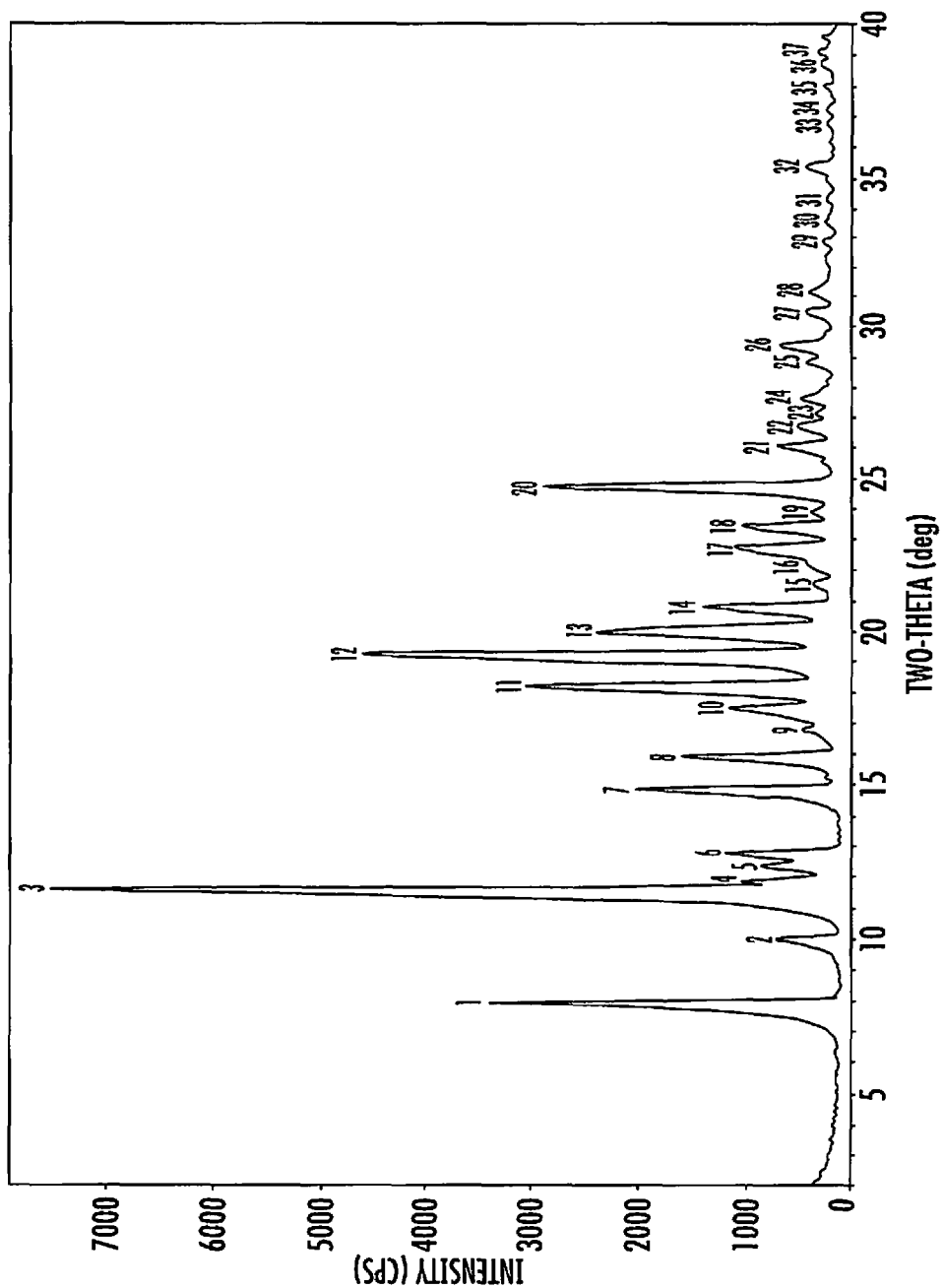

FIG. 3: X-ray diffraction pattern of crystalline (4R,6S)-(E)-6-[2-(2-cyclopropyl-4-(4-fluorophenyl)-quinoline-3-yl)-vinyl-2,2-dimethyl-1,3-dioxane-4-yl]acetic acid tertiary butyl ester compound (II).

Figure 4:
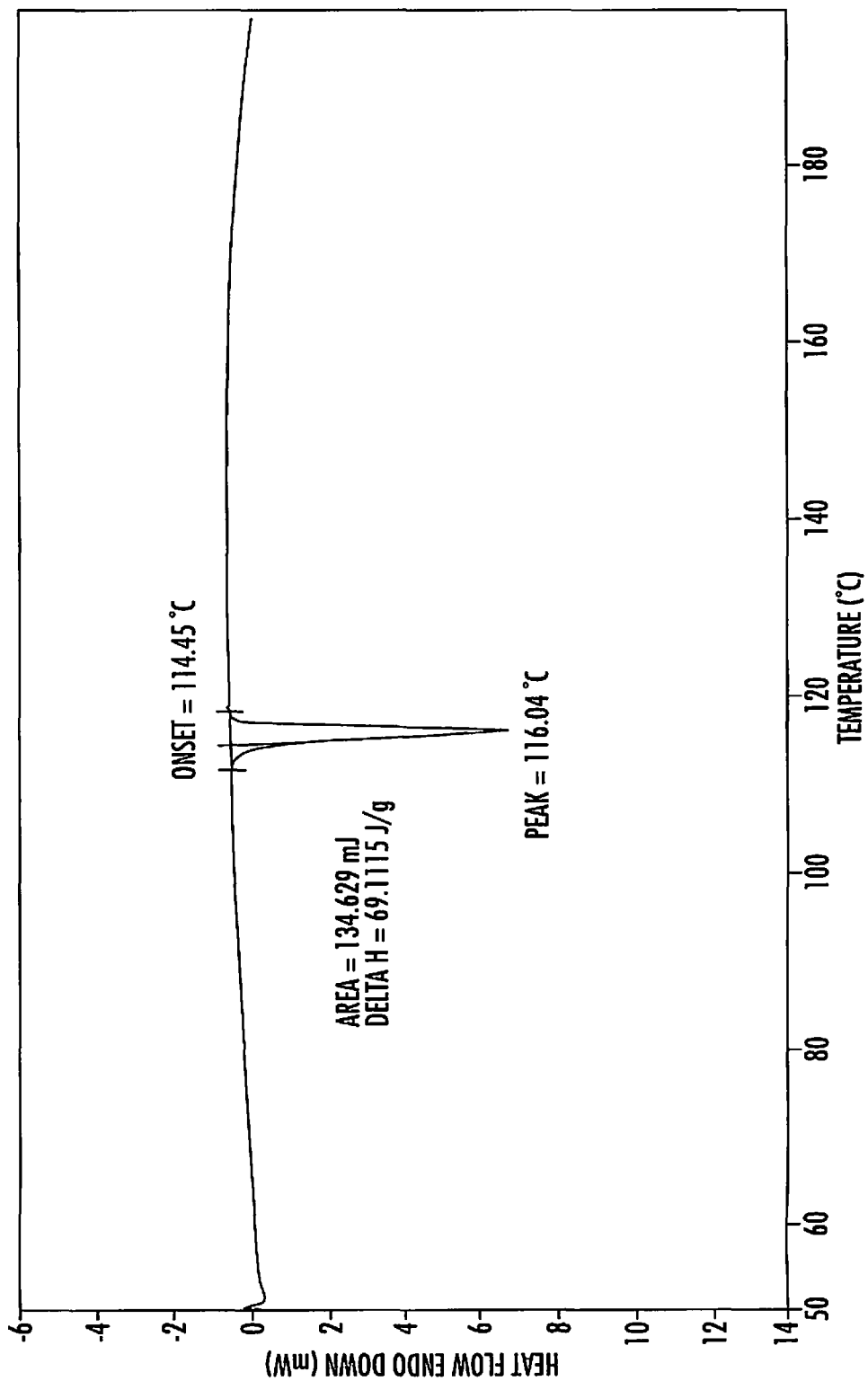

FIG. 4. DSC thermogram of crystalline (4R,6S)-(E)-6-[2-(2-cyclopropyl-4-(4-fluorophenyl)-quinoline-3-yl)-vinyl-2, 2-dimethyl-1,3-dioxane-4-yl]acetic acid tertiary butyl ester compound (II) having endothermic peak at about 116.04° C.

The details of one or more embodiments of the inventions are set forth in the description below.

Other features, objects and advantages of the inventions will be apparent from the description and claims.

DETAILED DESCRIPTION OF THE INVENTION

The prior art discloses the use of organic amine salts of Pitavastatin for obtaining better purity. The present inventors have found that pitavastatinalkali or alkaline earth metal salt prepared by using the process provided herein provides better yield and purity and avoids the use of amine salt formation. This significantly improves the process economics and commercial viability.

As used here in the term "isolation" may include filtration, filtration under vacuum, centrifugation, and decantation. The product obtained may be further or additionally dried to achieve the desired moisture values. For example, the product may be dried in a tray drier, dried under vacuum and/or in a Fluid Bed Drier.

Optionally, the solution, prior to any solids formation, can be filtered to remove any undissolved solids, solid impurities and the like prior to removal of the solvent. Any filtration system and filtration techniques known in the art can be used.

The term "Suitable organic solvent" means a single or a combination of two or more solvents.

The term "Substantially pure" means pitavastatinalkali or alkaline earth metal prepared by the process of the present invention is substantially free from any single individual impurities like desfluoro impurity, cis-isomer impurity, Pitavastatin 5-oxo impurity, pitavastatinlactone impurity, pitavastatin t-butyl diol ester impurity, and pitavastatincondensed impurity.

Further the term "substantially pure" means pitavastatinalkali or alkaline earth having purity greater than 99%. In particular, it may be greater than 99.5% by area percentage of HPLC. In particular, containing less than about 0.1% of single individual impurity as herein described above and total impurities not more than 1.0% by area percentage of HPLC.

Particularly, pitavastatindiastereomeric impurity and pitavastatinenantiomeric impurity are present less than about 0.3% by area percentage of HPLC.

The above impurities are present in the preparation of pitavastatinalkali or alkaline earth metal salts includes the following which were determined from an HPLC analysis of different batches of pitavastatinalkali or alkaline earth metal salts produced by the method described in the specification herein after:

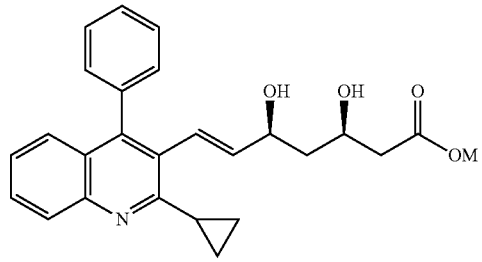

Des-Flouro Pitavastatin

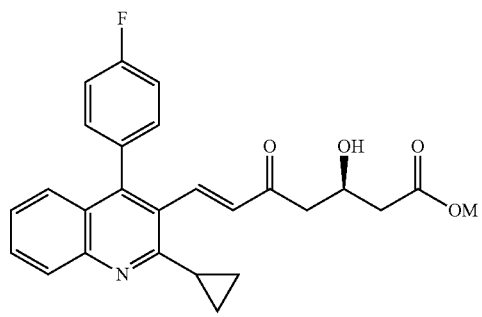

Pitavastatin 5-oxo Impurity

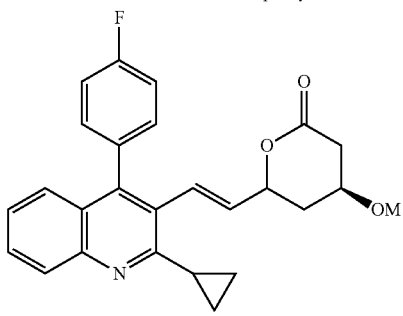

Pitavastatin Lactone Impurity

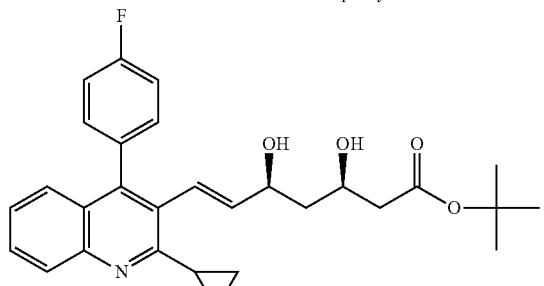

Pitavastatin t-butyl diol ester Impurity

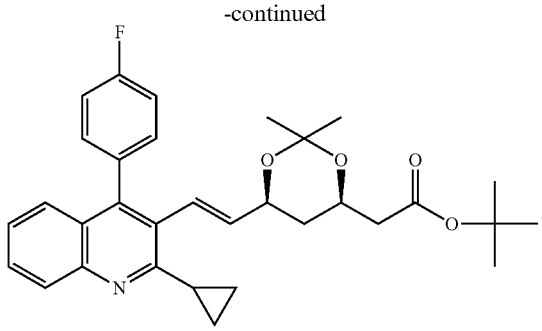

Pitavastatin Condensed Impurity

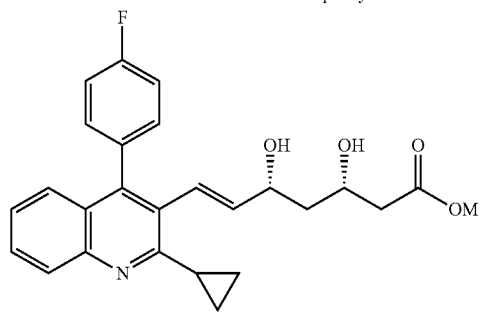

Pitavastatin Diastereomer Impurity

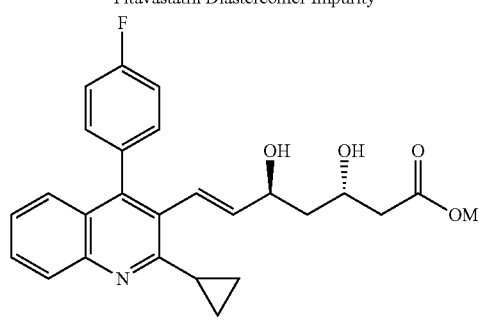

Pitavastatin Enantiomeric Impurity

In first embodiment, there is provided alkali or alkaline earth metal salts of pitavastatin, wherein the alkali or alkaline earth metal comprises one or more of magnesium, zinc, potassium, strontium, barium and the like. In particular, it may comprises one or more of magnesium, zinc and potassium.

In second embodiment of the present invention, there is provided a novel salt pitavastatin magnesium of Formula (IB)

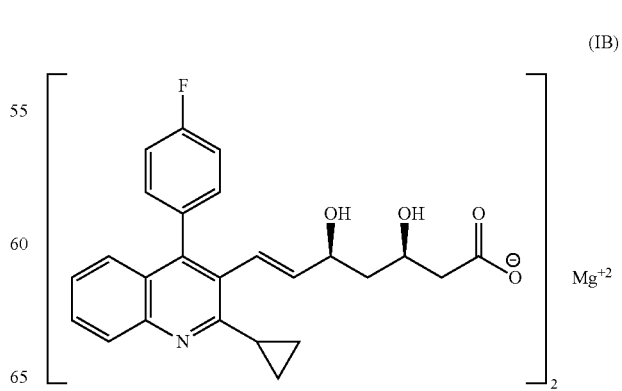

(IB)

In particular, the pitavastatin magnesium may be a hydrate having water content in the range of from about 7% to about 12% wt/wt. In particular, the water content may be about 9% to about 12% wt/wt. More particularly, the water content may be about 10% to about 12% wt/wt as measured by the known techniques in the art like Karl-Fisher method.

In yet another embodiment, there is provided pitavastatin magnesium in crystalline form having x-ray powder diffraction peaks at 10.1, 13.2, 19.3 and 27.2±0.2 (2θ). In particular, the pitavastatin magnesium crystalline form is having an x-ray powder diffraction pattern as shown in FIG. 1. Further embodiment includes pitavastatin magnesium having optical rotation of about +22.0 to +22.5 in 1% DMSO at 20±0.5° C.

In yet another embodiment, there is provided an amorphous form of the pitavastatin magnesium having x-ray powder diffraction peaks as shown in FIG. 2.

According to further embodiment, the amorphous form of pitavastatin magnesium is having the water content less than about 5% wt/wt. In particular, it may have the water content less than about 2% wt/wt.

In a third embodiment, there is provided a process for the preparation of pitavastatin and its pharmaceutically acceptable salts, in particular pitavastatin alkali or alkaline earth metal comprises one or more of magnesium, potassium, zinc and the like.

The pitavastatin alkali metal salts is chemically known as (3R,5S)-7-[2-cyclopropyl-4-(4-fluorophenyl)quinolin-3-yl]-3,5-dihydroxy-6(E)-heptenoic acid salt having the general Formula (I)

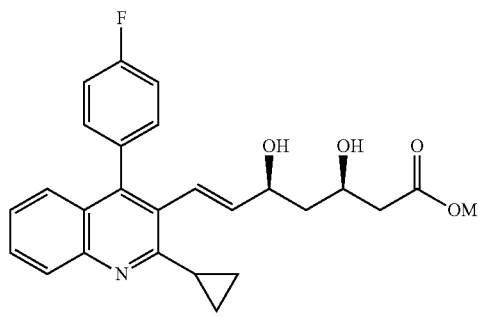

(I)

wherein, M is Na+, K+, Li+.

In a further embodiment of the present invention, there is provided a pitavastatin zinc of Formula (IC)

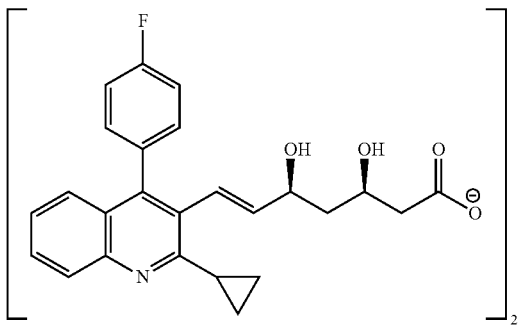

(IC)

In yet another aspect of the present invention, there is provided a pitavastatin potassium of formula (ID)

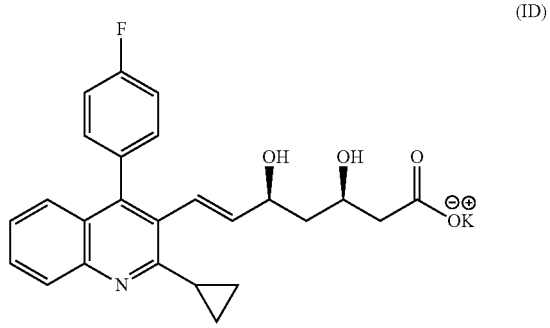

(ID)

According to a further embodiment, there is provided a process for the preparation of pitavastatin magnesium of formula (1B),

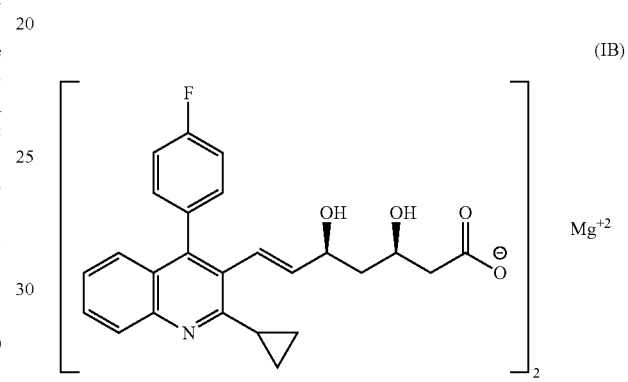

(IB)

the process comprising:
(a) reacting phosphonium bromide compound of Formula-IV

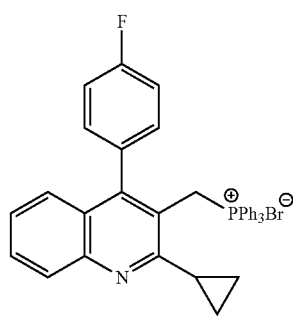

(IV)

with an aldehyde compound of Formula-III

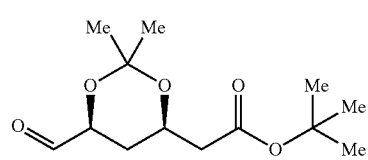

(III)

in the presence of an alkali or alkaline earth metal base in one or more suitable polar aprotic solvent to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of formula-II,

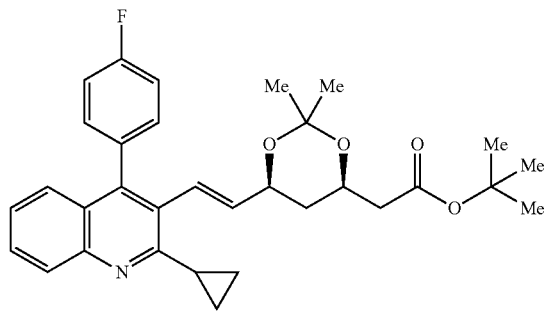

(II)

(b) hydrolyzing the compound of Formula-II under the acidic conditions to remove acetonide protection to form diol compound;
(c) treating the diol compound of step (b) in-situ with an alkali metal hydroxide to form the corresponding alkali metal salt of Pitavastatin (I);

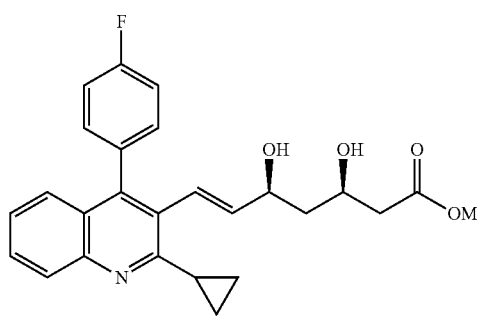

(I)

wherein, M is $Na^+$, $K^+$, $Li^+$;
(d) treating the alkali metal salt of pitavastatin (I) with a magnesium source to obtain pitavastatinmagnesium; and
(e) isolating the pitavastatin magnesium.

The phosphonium bromide compound of Formula-IV and aldehyde compound of Formula-III can be reacted in the presence of alkali or alkaline earth metal bases. The alkali or alkaline earth metal bases comprises one or more of sodium hydroxide, potassium hydroxide, lithium hydroxide, potassium carbonate, sodium carbonate, lithium carbonate, cesium carbonate and the like. In particular, it may be potassium carbonate.

Embodiments includes that the reaction may be performed in a suitable polar aprotic solvent comprises one or more dimethylformamide, dimethylsulfoxide, dimethylacetamide, tetrahydrofuran, N-methylpyrrolidone or mixtures thereof. In particular, it may be dimethylsulfoxide. The reaction may be performed at an ambient temperature i.e. at about 15° C. to about 40° C. In particular, it may be from about 20° C. to about 35° C.

The reaction mixture may be stirred for about 5 to 15 hours till completion of the reaction, in particular for 10 hours. The reaction mixture may be further treated with suitable organic solvents like toluene, xylene, methylene dichloride, ethyl acetate for extracting the compound of Formula-II. Particularly, the compound of Formula-II is extracted by using toluene.

In general, the compound of Formula-II may be isolated by removal of toluene followed by addition of isopropanol. After the addition of isopropanol, the reaction mixture can be heated to 40° C. to 80° C., preferably 60° C. to 70° C. and cooling to 15° C. to obtain olefin compound of Formula (II). The compound of Formula (II) may optionally be purified in suitable polar solvent like methanol, ethanol, Isopropanol, acetone, DMF, ethyl acetate, butyl acetate and the like. In particular, the compound of Formula (II) may be purified using methanol.

Further embodiments of the process include, hydrolysis of compound of Formula (II). The hydrolysis of olefin compound is done under the acidic conditions to remove the acetonide protection and to form diol compound. The suitable acids comprise one or more of hydrochloric acid, acetic acid, sulfuric acid, nitric acid, phosphoric acid and the like. In particular it may be hydrochloric acid.

The diol compound obtained is in-situ treated with an alkali metal hydroxide selected from sodium hydroxide, potassium hydroxide, lithium hydroxide and the like.

In particular it may be sodium hydroxide to obtain corresponding alkali metal salt of pitavastatin (I)

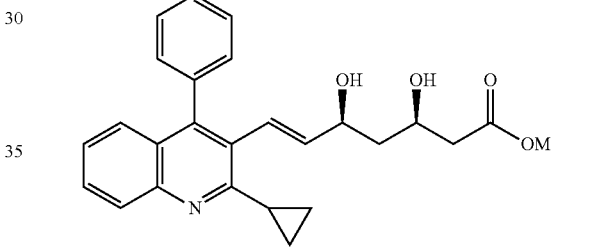

(I)

herein M is $Na^+$.

Embodiments of the process includes treating alkali metal salt of formula (I) of pitavastatin, in particular it may be pitavastatinsodium with magnesium source. Preferred magnesium source comprises one or more of magnesium chloride, magnesium methoxide, magnesium acetate and hydrates thereof. In particular, it may be magnesium chloride hexahydrate.

In general, the pitavastatinmagnesium prepared by the method as described above, can be dried in hot air oven at 40° C. to 45° C. for at least about 4 to 24 hours having water content in the range of about 8% to 12% wt/wt to obtain pitavastatinmagnesium in crystalline form.

Embodiments further includes, drying pitavastatin magnesium having water content in the range of about 8% to about 12% wt/wt for about 8 hours or more; in particular, for at least about 24 hours so as obtain substantially anhydrous pitavastatin magnesium having water content less than about 2% wt/wt.

According to the preferred embodiment, there is provided an improved process for the preparation of (4R,6S)-(E)-6-[2-(2-cyclopropyl-4-(4-fluorophenyl)quinoline-3-yl)-vinyl-2, 2-dimethyl-1,3-dioxane-4-yl]acetic acid tertiary butyl ester of Formula (II),

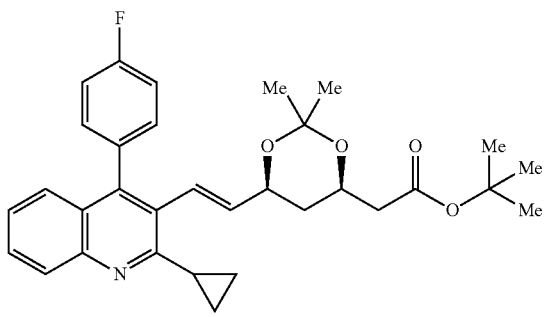

the process comprising:
(a) reacting phosphonium bromide compound of Formula-IV with an aldehyde compound of Formula-III in the presence of an alkali or alkaline earth metal base in one or more suitable polar aprotic solvent to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of Formula-II,
(b) treating compound of Formula-II with one or more suitable polar solvent to form reaction mixture;
(c) heating the reaction mixture at an elevated temperature;
(d) cooling the reaction mixture to ambient temperature; and
(e) isolating the (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester in crystalline form.

The phosphonium bromide compound of Formula-IV and aldehyde compound of Formula-III can be reacted in the presence of alkali or alkaline earth metal base. The alkali or alkaline earth metal base comprises one or more of sodium hydroxide, potassium hydroxide, lithium hydroxide, potassium carbonate, sodium carbonate, lithium carbonate, cesium carbonate and the like. In particular, it may be potassium carbonate.

Embodiments includes that the reaction can be performed in one or more of suitable polar aprotic solvent selected from dimethylformamide, dimethylsulfoxide, dimethylacetamide, tetrahydrofuran, N-methylpyrrolidone or mixtures thereof. In particular it may be dimethylsulfoxide at an ambient temperature i.e. at about 15° C. to about 40° C. In particularly, it may be from about 20° C. to about 35° C.

The reaction mixture can be stirred for about 5 to 15 hours till completion of the reaction. In particular, it may be for 10 hours. The reaction mixture can be further treated with suitable organic solvents like toluene, xylene, methylene dichloride, ethyl acetate for extracting compound of Formula-II. In particular, the compound of Formula (II) may be extracted with toluene.

The compound of Formula-II can be isolated by removal of toluene followed by addition of isopropanol. After the addition of isopropanol, the reaction mixture can be heated to 40° C. to 80° C., particularly at about 60° C. to 70° C. and cooling to 15° C. to obtain compound of formula (II). The compound of formula (II) can be purified in suitable polar solvent like methanol, ethanol, Isopropanol, acetone, DMF, ethyl acetate, butyl acetate and the like. In particular, it may be methanol.

In general, the term "elevated temperature" includes heating the compound II in a polar solvent at about 50° C. to about 100° C. In particular, the compound II may be heated at about 50° C. to about 70° C., most particularly, at about 60° C. to 65° C.

In general, the term "ambient temperature" includes cooling the reaction mixture comprising the compound II in a polar solvent at about 0° C. to about 30° C. In particular, it may be at about 0° C. to about 15° C., most particularly, at about 0° C. to 10° C. According to the embodiment, the compound (II) i.e. (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester is obtain in crystalline form after purification in polar solvent.

The crystalline form of compound (II) is characterized by an X-ray powder diffraction pattern having characteristics peaks expressed in degrees 2θ (±0.2° 2θ) at 7.86°, 9.94°, 11.48°, 12.71°, 14.80°, 15.88°, 17.44°, 18.16°, 19.17°, 19.97°, 20.77°, 22.71°, 23.41°, 24.68°, 26.02°, 27.63° and 29.36°±0.2°. The X-ray powder diffraction pattern is characterized substantially the same that shown in FIG. 3.

The crystalline form of compound (II) is characterized by an IR spectrum having peaks at about 2999, 2976, 1720, 1600, 1512, 1487, 1379, 1342, 1288, 1197, 1134, 1066, 1035, 931 and 842 cm$^{-1}$ and DSC endotherm at about 116.04° C. The DSC thermogram is substantially the same that shown in FIG. 4.

According to the further embodiment, there is provided a process for the preparation of pitavastatinzinc of formula (IC),

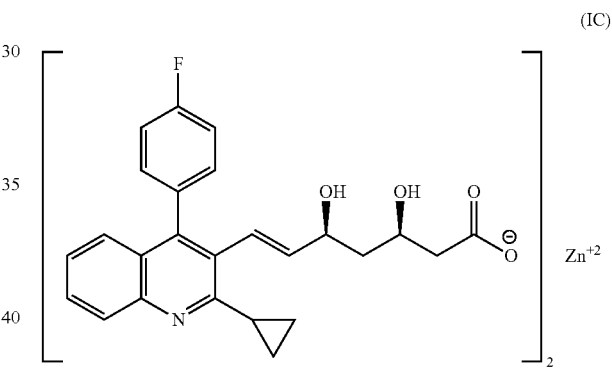

the process comprising:
(a) reacting phosphonium bromide compound of Formula-IV with an aldehyde compound of Formula-III in the presence of an alkali or alkaline earth metal base in one or more suitable polar aprotic solvent to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of formula-II;
(b) hydrolyzing the compound of Formula-II under the acidic conditions to remove the acetonide protection to form diol compound;
(c) treating the diol compound of step (b) in-situ with an alkali metal hydroxide to form the corresponding alkali metal salt of pitavastatin (I);
(d) treating the alkali metal salt of pitavastatin (I) with a zinc source to obtain Pitavastatinzinc; and
(e) isolating the pitavastatinzinc.

In general, the process parameters for the preparation of compound (II) and its hydrolysis are similar as discloses herein above. The preferable zinc source comprises one or more of zinc formate, zinc acetate, zinc propionate, zinc maleate, zinc fumarate, zinc tartrate, zinc lactate, zinc malate, zinc citrate, Zinc ascorbate, zinc malonate, zinc oxalate, zinc glycolate, zinc methanesulfonate, zinc ethanesulfonate, a salt of zinc with amino acid, zinc sulfate, zinc chloride, zinc carbonate or zinc nitrate. In particular, it comprises one or more of zinc sulfate, zinc chloride or zinc acetate.

According to the further aspect, there is provided a method for the preparation of pitavastatinpotassium of formula (ID),

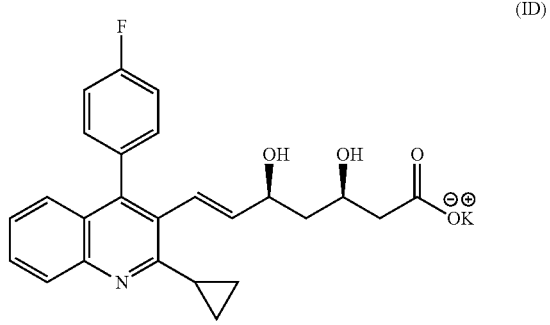

the process comprising:
(a) reacting phosphonium bromide compound of Formula-IV with an aldehyde compound of Formula-III in the presence of an alkali or alkaline earth metal bases in one or more suitable polar aprotic solvent to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of Formula-II,
(b) hydrolyzing the compound of Formula-II by subjecting under the acidic conditions to remove the acetonide protection to form diol compound;
(c) treating the diol compound of step (b) in-situ with a potassium source to obtain pitavastatinpotassium.

In general, the process parameters for the preparation of compound (II) and its hydrolysis are similar as discloses herein above. The preferable potassium source comprises one or more of potassium hydroxide, potassium carbonate, potassium bicarbonate, potassium acetate, potassium chloride and the like.

According to the further embodiment, there is provided a process for the preparation of amorphous form of pitavastatinmagnesium, the process comprising:
(a) providing a solution comprising pitavastatinmagnesium in a suitable organic solvent wherein the organic solvent is selected from the group consisting of a chlorinated solvent, alcoholic solvent, ketonic solvent, esters solvent and mixtures thereof;
(b) removing the organic solvent to obtain residue;
(c) adding a suitable anti-solvent to the residue; and
(d) recovering the amorphous form of the pitavastatinmagnesium.

The amorphous form can be generally prepared by addition of anti-solvent to a concentrated solution of pitavastatinmagnesium in an organic solvent.

Embodiments of the process includes preparing the solution of pitavastatinmagnesium in suitable organic solvent selected from the group consisting of a chlorinated solvent, alcoholic solvent, ketonic solvent, ester solvents and mixtures thereof. The preferred solvent comprises one or more of methylene dichloride, ethylene dichloride, chlorobenzene, methanol, ethanol, isopropanol, butanol, acetone, methylethyl ketone, ethyl acetate, butyl acetate, isopropyl acetate, and mixtures thereof or mixture thereof with water. In particular, the suitable solvent comprises one or more of methanol, acetone, ethyl acetate.

In general, the embodiment of the process includes adding suitable antisolvent to the solution of pitavastatinmagnesium in suitable organic solvent. The suitable anti-solvent comprises one or more of hexane, heptane, cyclohexane, toluene, xylene, diisopropyl ether, methyl tert-butyl ether, 1,4-dioxane, tetrahydrofuran and the like. In particular, the suitable anti-solvent comprises one or more of heptane or cyclohexane or methyl tert-butyl ether.

According to the embodiment, there is provided a process for the preparation of amorphous form of pitavastatinmagnesium, the process comprising:
(a) providing a solution comprising pitavastatinmagnesium in a suitable organic solvent wherein the organic solvent is one or more of a chlorinated solvent, alcoholic solvent, ketonic solvent, esters solvent and mixtures thereof;
(b) heating reaction mixture at an elevated temperature followed by cooling to ambient temperature;
(c) adding a suitable anti-solvent to the solution; and
(d) recovering the amorphous form of pitavastatinmagnesium.

In general, the suitable solvents and anti-solvents comprises from the same as listed herein above. However, the reaction mixture can be heated to an elevated temperature in step (b). The elevated temperature is from about 50° C. to about 100° C. In particularly, it may be from about 70° C. to about 90° C.

The reaction mixture is then cooled to an ambient temperature, preferably from about 15° C. to about 35° C., preferably from about 25° C. to 35° C.

It is preferable that the anti-solvent and solvent are miscible. The amorphous form can also be prepared by lyophilization of or removal of solvent from the solution of pitavastatinmagnesium in a suitable solvent.

According to the further embodiments, there is provided a process for the preparation of amorphous form of pitavastatinmagnesium having water content less than about 2% wt/wt, the process comprising:
(a) providing pitavastatinmagnesium in crystalline form having water content in the range of about 8% to about 12% wt/wt;
(b) contacting the pitavastatinmagnesium with humid air in a fluidized bed drier, or maintaining the pitavastatinmagnesium at a temperature of from about 5 to about 60° C., under pressure of less than 30 mm/Hg for a period of from about 1 to 5 days; and
(c) recovering the pitavastatin magnesium in the amorphous form having water content less than about 2% wt/wt.

According to the process, amorphous form of pitavastatinmagnesium having water content less than about 2% wt/wt is prepared by contacting pitavastatinmagnesium containing about 8% to about 12% of water content with humid air in a fluidized bed apparatus.

In particular, the temperature is of about 25° C. to about 50° C., more particularly at about 30° C. to about 40° C. The contacting may be carried out, in particularly at about 6 hours to 2 days. As used herein, the term "humid" refers to a relative humidity of at least 30%. In particular, it may be at least about 50% and most particularly at least about 70%.

According to the further embodiment, there is provided substantially pure pitavastatinmagnesium in stable crystalline form.

In another embodiment, there is provided pitavastatinmagnesium substantially free desfluoro impurity, cis-isomer impurity, pitavastatin 5-oxo impurity, pitavastatinlactone impurity, pitavastatin t-butyl diol ester impurity and pitavastatincondensed impurity when measured by area percentage of HPLC. Also, pitavastatin diastereomeric impurity less than 0.3% by area percentage of HPLC.

According to the further embodiment, there is provided a pharmaceutical composition comprising a therapeutically effective amount of crystalline pitavastatinmagnesium characterized by X-ray diffraction pattern having characteristic peaks at 2-theta values 10.1°, 13.2°, 19.3° and 27.2°±0.2°, and one or more pharmaceutically acceptable carriers, excipients or diluents.

According to the further embodiment, there is provided a pharmaceutical composition comprising a therapeutically effective amount of amorphous pitavastatinmagnesium characterized by x-ray diffraction pattern substantially as depicted in FIG. 2, and one or more pharmaceutically acceptable carriers, excipients or diluents.

The starting material, phosphonium bromide compound of Formula-IV, can be prepared from alcoholic compound of formula (VI)

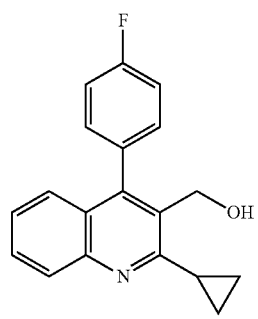

(VI)

The alcoholic compound of formula (VI) is converted o phosphonium compound of Formula (IV) via formation of 3-(bromomethyl)-2-cyclopropyl-4(4'-fluorophenyl)quinoline of Formula (V) by the known process reported in the prior art. WO 95/11898 A1 in its reference example-7 and Example-1 or as per the process disclosed in U.S. Pat. No. 6,627,636 and U.S. Pat. No. 5,763,675.

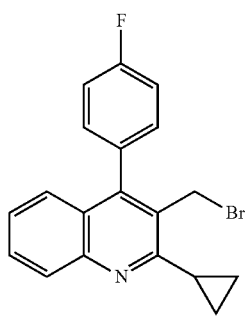

(V)

The bromo compound of formula (V) 3-(bromomethyl)-2-cyclopropyl-4-(4'-fluorophenyl)quinoline with wittig reagent like triphenyl phosphine in suitable non-polar solvents like toluene, o-xylene, chlorobenzene etc to obtain phosphonium bromide compound of formula (IV).

The starting reagent, alcohol compound of formula (VI) can be prepared from the known process reported in the art like *Tetrahedron Letters*, Vol. 34, No. 51, p.p. 8271-8274 (1993); *Heterocycles*, Vol. 50, No. 1, 1999; *Drugs of Future* 1998 23 (8) or *Tetrahedron Asymmetry* 1993, Vol. 4, pp. 201-204 are reported herein as reference in its entirety.

As set forth in the following schemes, the pitavastatin magnesium can be prepared by as shown bellow:

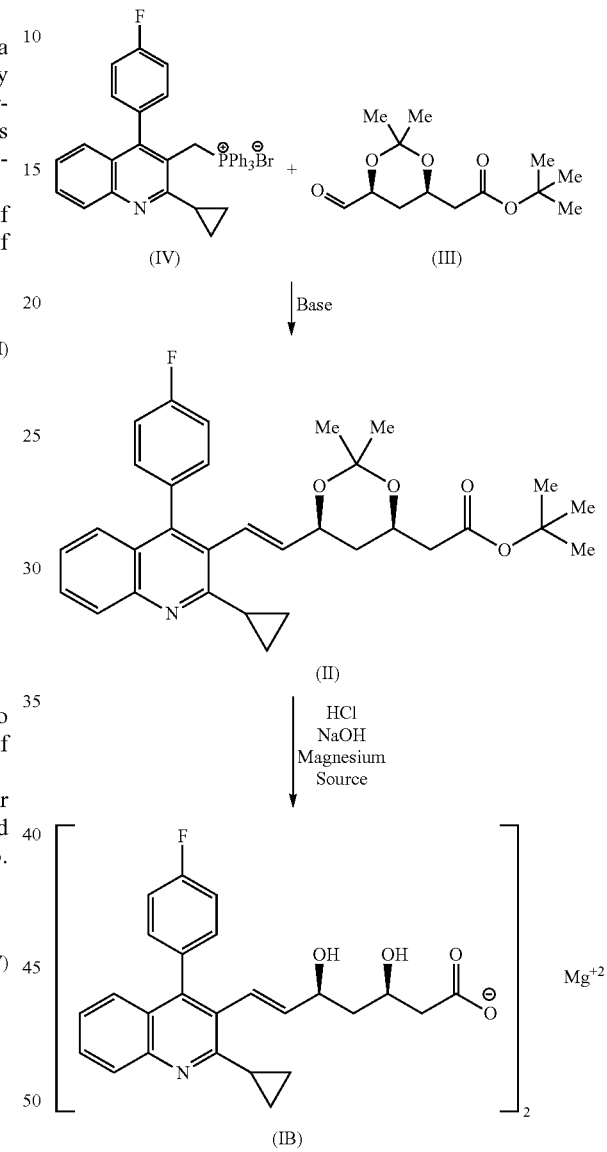

The present invention is further illustrated by the following examples which are provided merely to be exemplary of the invention and do not limit the scope of the invention. Certain modifications and equivalents will be apparent to those skilled in the art and are intended to be included within the scope of the present invention.

Preparation-1

Preparation of 3-(bromomethyl)-2-cyclopropyl-4-(4'-fluorophenyl)quinoline (V)

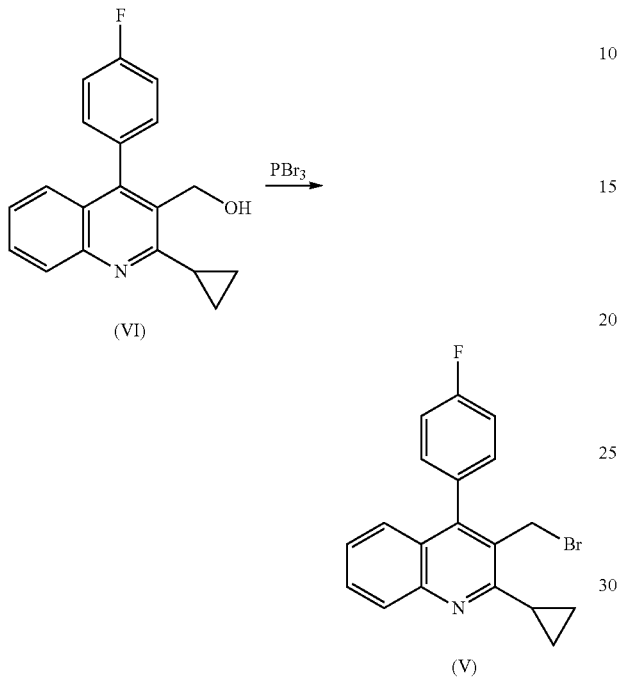

1 Kg of alcohol compound of formula (VI) and 8 L of methylene dichloride were taken in reactor at 0° C. 0.462 Kg of freshly prepared phosphonium bromide solution in 2 L methylene dichloride was added slowly and stirred at 25° C. for 2 hours. After the completion of the reaction as monitored by TLC, the reaction mixture was quenched with 5% sodium bicarbonate solution to adjust the pH from 7-8. The organic layer was separated and washed with 5 L water followed by removal of solvent under vacuum at 45° C. The residue was treated with 2.5 L heptane at 60° C. and cooled to 15° C. The product was filtered at 15° C. and dried under vacuum at 55° C. for 8 hours to obtain 3-(bromomethyl)-2-cyclopropyl-4-(4'-fluorophenyl)quinoline.

Preparation-2

Preparation of Phosphonium Bromide Compound of Formula (IV)

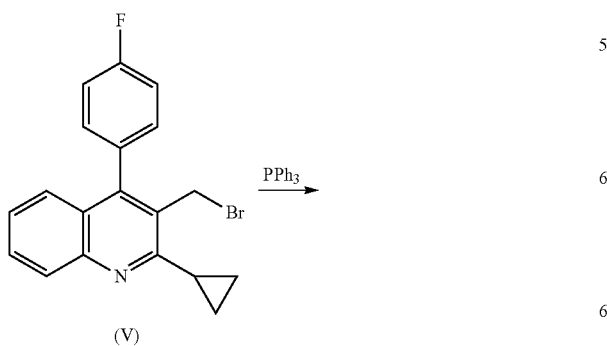

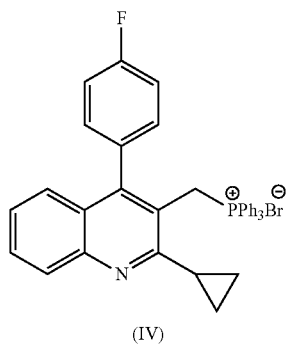

1 Kg of 3-(bromomethyl)-2-cyclopropyl-4-(4'-fluorophenyl)quinoline, 10 L of toluene and 300 mL of isopropanol were taken in reactor and heated at 50° C. 0.874 Kg of triphenyl phosphine solution in 2 L toluene was added slowly and stirred for 3 hours. The reaction mixture was cooled to 25° C. and stirred for 1 hour. The product was filtered and washed with toluene. The product was dried in tray dryer at 55° C. for 8 hours to obtain phosphonium bromide compound of formula (IV).

Example-1

Preparation of (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester Compound of Formula II

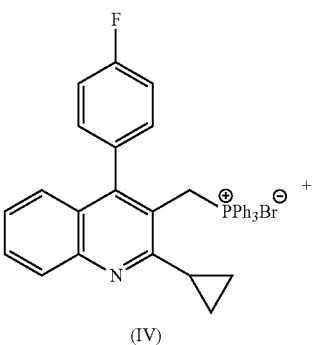

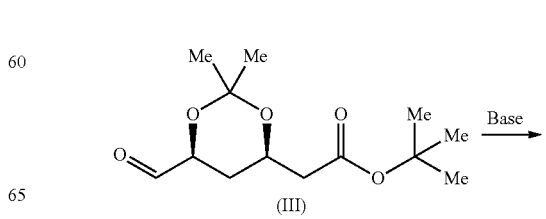

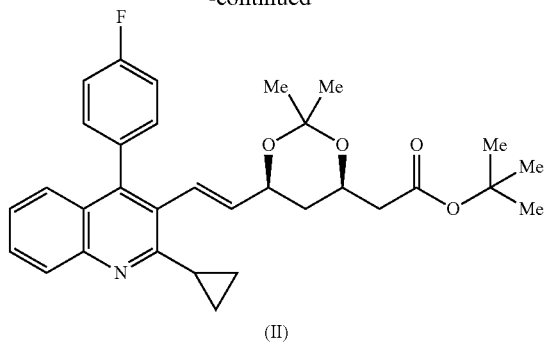

(II)

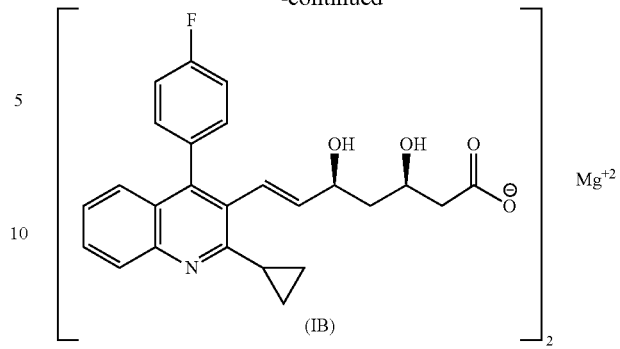

(IB)

To the solution of 0.751 Kg of tert-butyl-2-((4R,6S)-6-formula-2,2-dimethyl-1,3-dioxan-4-yl)acetate (III) in 7 L of dimethylsulphoxide was added 1 Kg of phosphonium bromide compound of formula (IV) and 0.67 Kg of potassium carbonate. The reaction mixture was stirred at 25° C. for 10 hours. The reaction mixture was quenched with water and extracted with toluene. The organic layer was concentrated and the title compound was isolated using isopropanol as crude solid. The crude product thus obtained was recrystallized in methanol as shown below.

Purification of Olefin Compound of Formula II

Pitavastatin Olefin compound (II) (100 g) and methanol (600 mL) were heated to 60° C. to 65° C. to obtain the clear solution and stirred for 10 mins. Activated Carbon (10 g) were added at 60° C. to 65° C. and stirred for 10 min. The reaction mixture was filtered and washed with methanol (100 mL). The filtrate was cooled to 25° C. and gradually to 10° C. followed by stirring for 2 hours at 10° C. The resulting slurry was filtered and washed with chilled methanol (100 mL). The wet-cake was heated in methanol (480 mL) at 60° C. to 65° C. to obtain the clear solution. Activated Carbon (10 g) were added at 60° C. to 65° C. and stirred for 10 min. The reaction mixture was filtered and washed with methanol (100 mL). The filtrate was cooled to 25° C. and gradually to 10° C. followed by stirring for 2 hours at 10° C. The resulting slurry was filtered and washed with chilled methanol (100 mL). The wet-cake was dried under vacuum for 30 minutes followed by drying in hot air oven at 50° C. to 55° C. for 12 hours to obtain crystalline olefin compound (II) characterized by X-ray powder diffraction substantially as same as shown in FIG. 3 and DSC thermogram having endothermic peak at about 116.04° C. as shown in FIG. 4.

Example-2

Preparation of Pitavastatin Magnesium of Formula (IB)

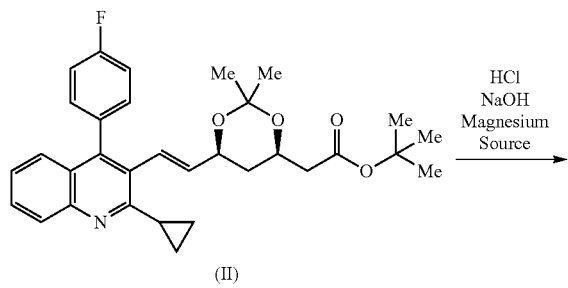

(II)

To the solution of 100 g of (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of formula II (crystalline) in 1 L methanol was added 272.8 mL 1N HCl solution at 25° C. The reaction mixture was stirred for 8 hours. The reaction mixture was cooled to 15° C. and treated with 23.2 g 10% sodium hydroxide solution.

The reaction mixture was stirred for 4 hours at 25° C. and quenched in water. The reaction mass was treated with 92 mL 1 N HCl solution to adjust the pH of about 8.0 and treated with methylene dichloride for washing. The separated aqueous layer is treated with 100 g of magnesium chloride hexahydrate and stirred for 30 min at 25° C. The solution is cooled to 15° C., filtered and washed with water. The product is dried in hot air oven for 4 hours to obtain 82 g of crystalline Pitavastatin Magnesium having water content of 11.0%. (XRD as shown in FIG. 1)

Example-3

Preparation of Pitavastatin Zinc of Formula (IC)

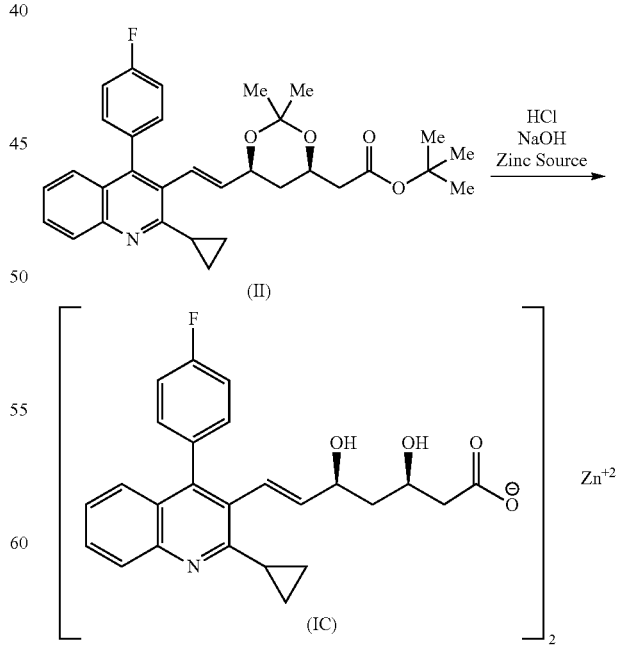

(II)

(IC)

To the solution of 100 g of (4R,6S)-(E)-6-[2-(2-cyclopropyl-4-(4-fluorophenyl)quinoline-3-yl)-vinyl-2,2-dimethyl- 1,3-dioxane-4-yl]acetic acid tertiary butyl ester compound of formula II (crystalline) in 1 L methanol was added 272.8 mL 1N HCl solution at 25° C. The reaction mixture was stirred for 8 hours. The reaction mixture was cooled to 15° C. and treated with 23.2 g 10% sodium hydroxide solution. The reaction mixture was stirred for 4 hours at 25° C. and quenched in water. The reaction mass was treated with 92 mL 1 N HCl solution to adjust the pH of about 8.0 and treated with methylene dichloride for washing. The separated aqueous layer is treated with 100 g of zinc sulfate and stirred for 30 min at 25° C. The solution is cooled to 15° C., filtered and washed with water. The product is dried in hot air oven for 4 hours to obtain 75 g of crystalline Pitavastatin zinc.

Example-4

Preparation of Pitavastatin Potassium of Formula (ID)

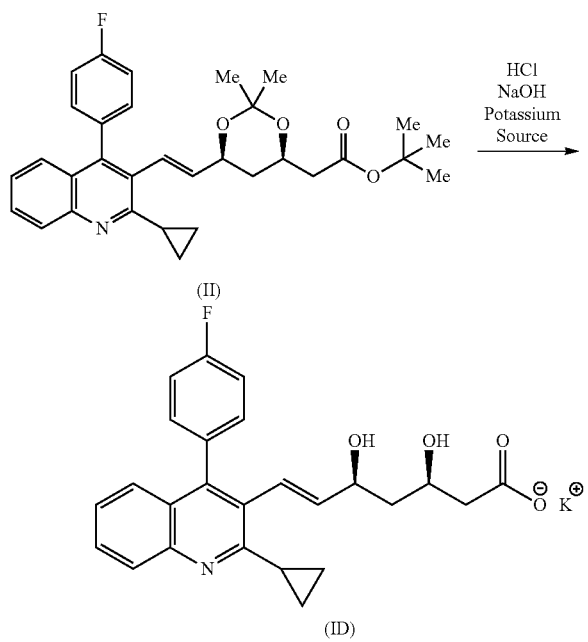

To the solution of 100 g of (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of formula II (crystalline) in 1 L methanol was added 272.8 mL 1N HCl solution at 25° C. The reaction mixture was stirred for 8 hours. The reaction mixture was cooled to 15° C. and treated with 23.2 g 10% sodium hydroxide solution. The reaction mixture was stirred for 4 hours at 25° C. and quenched in water. The reaction mass was treated with 92 mL 1 N HCl solution to adjust the pH of about 8.0 and treated with methylene dichloride for washing. The separated aqueous layer is treated with 80 g of Potassium hydroxide and stirred for 30 min at 25° C. The solution is cooled to 15° C., filtered and washed with water. The product is dried in hot air oven for 4 hours to obtain 72 g of crystalline Pitavastatin Potassium.

Example 5

Preparation of the Amorphous Form of Pitavastatin Magnesium 100 g of crystalline Pitavastatin Magnesium was dissolved in 800 ml Ethyl Acetate by heating at 75° C. to 80° C. The slightly turbid solution was filtered through hyflow bed at 75° C. to 80° C. The filtrate was cooled to 25° C. and added to cyclohexane (3300 mL). The reaction mixture was stirred for 2 hours. The reaction mixture was filtered and wet-cake was washed with cyclohexane (100 mL). The product was dried in hot air oven for 12 hours to get 83.0 g amorphous Pitavastatin Magnesium. The obtained solid was amorphous as is shown by the X-ray diffraction pattern given in FIG. 2.

Example 6

Preparation of the Amorphous Form of Pitavastatin Magnesium 100 g of crystalline Pitavastatin Magnesium was dissolved in 800 ml Ethyl Acetate by heating at 75° C. to 80° C. The slightly turbid solution was filtered through hyflow bed at 75° C. to 80° C. The filtrate was distilled under vacuum till dry powder obtained at 45° C. to 50° C. The solid was cooled to 25° C. and cyclohexane (500 mL) was added to the filtrate and stirred for 30 min. The reaction mixture was filtered and wet-cake was washed with cyclohexane (100 mL). The product was dried in hot air oven for 12 hours to get 83.0 g amorphous Pitavastatin Magnesium. The obtained solid was amorphous as is shown by the X-ray diffraction pattern given in FIG. 2.

Example 7

Preparation of the Amorphous Form of Pitavastatin Magnesium 100 g of crystalline Pitavastatin Magnesium and Methanol (500 mL) were stirred in RBF for 30 minutes. The reaction mixture was distilled at 45° C. to 50° C. under vacuum to obtain dry product. The filtrate was distilled under vacuum till dry powder obtained at 45° C. to 50° C. The solid was cooled to 25° C. and cyclohexane (500 mL) was added to the filtrate and stirred for 30 min. The reaction mixture was filtered and wet-cake was washed with cyclohexane (100 mL). The product was dried in hot air oven for 12 hours to get 83.0 g amorphous Pitavastatin Magnesium.

Example 8

Preparation of the Amorphous Form of Pitavastatin Magnesium 100 g of crystalline Pitavastatin Magnesium was dissolved in 800 ml Acetone by heating at 55° C. to 60° C. The slightly turbid solution was filtered through hyflow bed at 55° C. to 60° C. The filtrate was cooled to 25° C. and added to diisopropyl ether (3000 mL). The reaction mixture was stirred for 3-min. The reaction mixture was filtered and wet-cake was washed with diisopropyl ether (100 mL). The product was dried in hot air oven for 12 hours to get 45.0 g amorphous Pitavastatin Magnesium.

Example 9

Preparation of the Amorphous Form of Pitavastatin Magnesium 100 g of Pitavastatin Magnesium having water content 11% was dried in fluid bed dried at 45° C. for 2 days to obtain amorphous Pitavastatin Magnesium having water content less than 2% wt/wt. An X-ray diffraction study on the product showed it to be amorphous.

Example 10

Preparation of the Amorphous Form of Pitavastatin Magnesium 100 g of Pitavastatin Magnesium having water content 11% was dried in vacuum tray dryer at about 5 to about 60° C., under pressure of less than 30 mm/Hg for a period of 24 hours to obtain amorphous Pitavastatin Magnesium having water content less than 2% wt/wt. An X-ray diffraction study on the product showed it to be amorphous, see FIG. 2.

While the present invention has been described in terms of its specific embodiments, certain modifications and equivalents will be apparent to those skilled in the art and are intended to be included within the scope of the present invention.

Advantages of the Invention

1. The present invention provides novel pharmaceutically acceptable salt of alkali metal salts of Pitavastatin.
2. The present invention provides an improved process for the preparation of pitavastatinalkali metal salts.
3. The present invention provides crystalline form of pitavastatinmagnesium having 8% to 12% water content.
4. The present invention also provides amorphous form of pitavastatinmagnesium and process for preparation thereof.
5. The present invention provides amorphous form of pitavastatinmagnesium containing less than about 2% of water content.
6. The process provided is eco-friendly, economically viable and easily scalable on large scale production.

We claim:

1. An isolated pitavastatin magnesium compound of Formula (IB) or a hydrate thereof

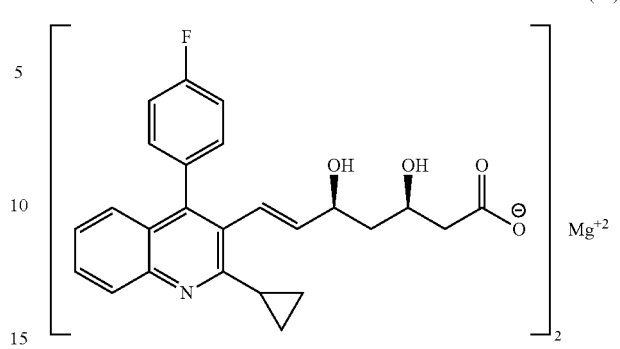

2. The compound as claimed in claim 1, wherein the compound has a water content in the range of from about 7% to about 12% wt/wt.

3. A crystalline pitavastatin magnesium compound of Formula (IB) or a hydrate thereof wherein the crystalline pitavastatin magnesium compound has an X-ray powder diffraction pattern having characteristic peaks expressed in degrees 2θ (±0.2° 2θ) at 10.1°, 13.2°, 19.3° and 27.2°±0.2°.

4. The compound as claimed in claim 3 having an x-ray powder diffraction pattern substantially same as that shown in FIG. 1.

5. The compound as claimed in claim 2, wherein the compound is amorphous.

6. An amorphous pitavastatin magnesium compound of Formula (IB) or a hydrate thereof having an x-ray powder diffraction pattern substantially the same as that shown in FIG. 2

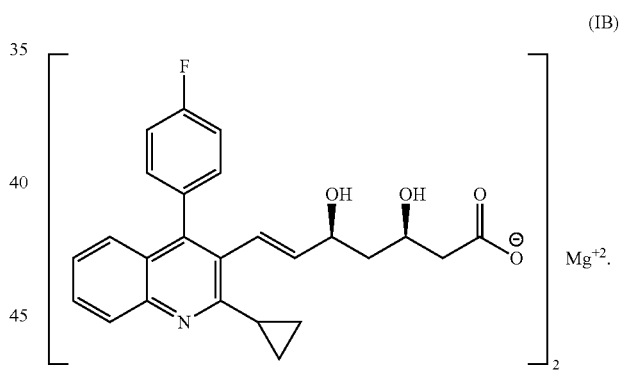

7. The compound as claimed in claim 5, wherein the compound has a water content less than about 5% wt/wt.

8. The compound as claimed in claim 5 having a specific optical rotation of about +22.0 to +22.5 in 1% DMSO at 20±0.5° C.

9. A pharmaceutical composition comprising pitavastatin magnesium of claim 5 and one or more pharmaceutically acceptable carriers or excipients.

10. The compound as claimed in claim 5, wherein the pitavastatin magnesium is substantially pure having purity greater than about 99% by area percentage of HPLC.

11. The compound as claimed in claim 5, wherein the pitavastatin magnesium is substantially pure having less than about 0.3% of diastereomeric impurity by area percentage of HPLC.

12. A process for the preparation of pitavastatin magnesium of Formula (IB) as claimed in claim 5, (IB)

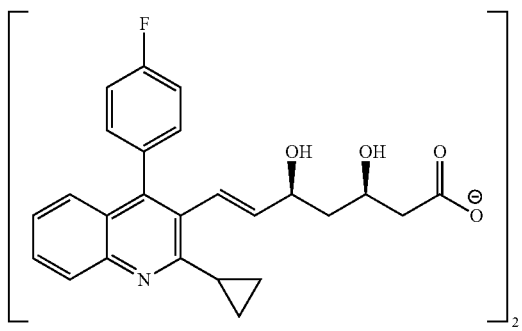

the process comprising:
(a) reacting phosphonium bromide compound of Formula-IV (IV)

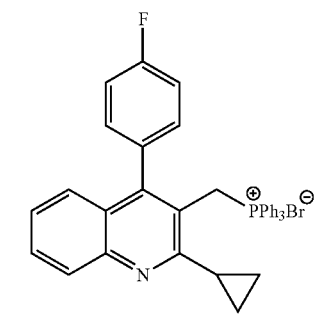

with an aldehyde compound of Formula-III (III)

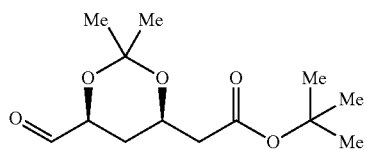

in the presence of an alkali or alkaline earth metal base in one or more suitable polar aprotic solvents to provide (4R,6S)-(E)-6-[2-(2-cyclopropyl-4-(4-fluorophenyl)quinoline-3-yl)-vinyl-2,2-dimethyl-1,3-dioxane-4-yl]acetic acid tertiary butyl ester compound of Formula-II;

(II)

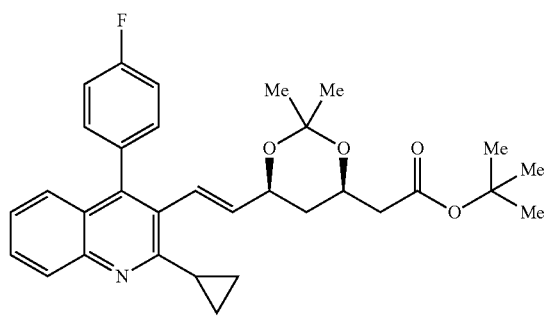

(b) hydrolyzing the compound of Formula-II under acidic conditions to remove acetonide protection to form a diol compound;

(c) treating the diol compound of step (b) in situ with an alkali metal hydroxide to form corresponding alkali metal salt of pitavastatin (I);

(I)

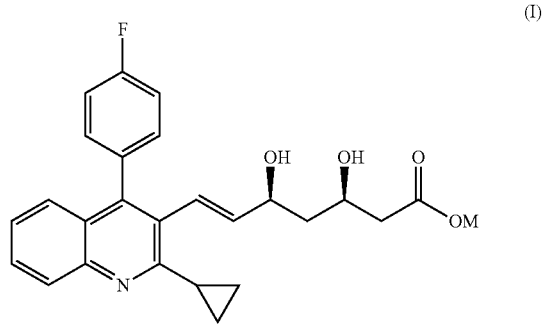

wherein, M is Na$^+$, K$^+$, Li$^+$;

(d) treating alkali metal salt of pitavastatin (I) with a magnesium source to obtain pitavastatin magnesium; and (e) isolating the pitavastatin magnesium.

13. The process as claimed in claim 12, wherein in step (a) the alkali or alkaline earth metal base comprises one or more of sodium hydroxide, potassium hydroxide, lithium hydroxide, potassium carbonate, sodium carbonate, lithium carbonate, and cesium carbonate.

14. The process as claimed in claim 12, wherein in step (a) the suitable polar aprotic solvent comprises one or more of dimethylformamide, dimethylsulfoxide, dimethylacetamide, tetrahydrofuran, N-methylpyrrolidone, or mixtures thereof.

15. The process as claimed in claim 12, wherein the compound (II) can optionally be isolated by removal of the solvent.

16. The process as claimed in claim 12, wherein the compound (II) can optionally be purified in a suitable polar solvent selected from methanol, ethanol, isopropanol, acetone, DMF, ethyl acetate, or butyl acetate.

17. The process as claimed in claim 12, wherein in step (b) the hydrolysis of compound (II) under acidic conditions can be done by selecting suitable acids from hydrochloric acid, acetic acid, sulfuric acid, nitric acid, and phosphoric acid.

18. The process as claimed in claim 12, wherein in step (c) the alkali metal hydroxide comprises one or more of sodium hydroxide, potassium hydroxide, and lithium hydroxide.

19. The process as claimed in claim 15, wherein in step (c) the alkali metal salt of pitavastatin is pitavastatin sodium.

20. The process as claimed in claim 12, wherein in step (d) the magnesium source comprises one or more of magnesium chloride, magnesium methoxide, magnesium acetate and hydrates thereof.

21. The process as claimed in claim 15, wherein in step (e) the pitavastatin magnesium is isolated in a crystalline form.

22. A crystalline pitavastatin magnesium compound of Formula (IB) or a hydrate thereof,

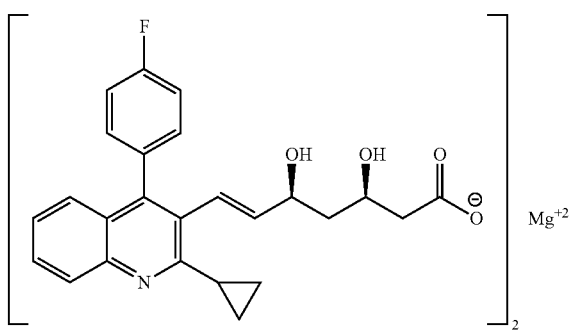

(IB)

wherein the pitavastatin magnesium compound has an X-ray powder diffraction pattern having characteristics peaks expressed in degrees 2θ (±0.2° 2θ) at 10.1°, 13.2°, 19.3° and 27.2°±0.2° and is characterized by one or more of:
(a) having a specific optical rotation of about +22.0 to +22.5 in 1% DMSO at 20±0.5° C.;
(b) having a purity greater than about 99% by area percentage of HPLC; and
(c) having less than about 0.3% of diastereomeric impurity by area percentage of HPLC.

23. A pitavastatin magnesium compound of Formula (IB) or a hydrate thereof, (IB)

wherein
the pitavastatin magnesium compound is crystalline and has an X-ray powder diffraction pattern having characteristics peaks expressed in degrees 2θ (±0.2° 2θ) at 10.1°, 13.2°, 19.3° and 27.2°±0.2°; or
the pitavastatin magnesium compound is crystalline and has an x-ray powder diffraction pattern substantially same as that shown in FIG. 1; or
the pitavastatin magnesium compound is amorphous and has an x-ray powder diffraction pattern substantially the same as that shown in FIG. 2.

24. The compound as claimed in claim 23, wherein the compound is crystalline and has a water content in the range of from about 7% to about 12% wt/wt.

25. The compound as claimed in claim 23, wherein the compound is amorphous and has a water content less than about 5% wt/wt.

26. The compound as claimed in claim 23, having a specific optical rotation of about +22.0 to +22.5 in 1% DMSO at 20±0.5° C.

27. The compound as claimed in claim 23, wherein the pitavastatin magnesium is substantially pure having a purity greater than about 99% by area percentage of HPLC.

28. The compound as claimed in claim 23, wherein the pitavastatin magnesium is substantially pure having less than about 0.3% of diastereomeric impurity by area percentage of HPLC.

29. A pharmaceutical composition comprising the pitavastatin magnesium of claim 23 and one or more pharmaceutically acceptable carriers or excipients.

30. The compound as claimed in claim 6, wherein the amorphous pitavastatin magnesium compound has a water content less than about 5% wt/wt.

* * * * *